United States Patent [19]
Okada et al.

[11] Patent Number: 5,834,212
[45] Date of Patent: Nov. 10, 1998

[54] ANTI-HUMAN STROMELYSIN MONOCLONAL ANTIBODY AND METHOD FOR DIAGNOSIS OF RHEUMATOID ARTHRITIS BY ENZYME IMMUNOASSAY

[76] Inventors: Yasunori Okada, 32, Wakamiya 2-chome, Matto-shi, Ishikawa-ken, 924; Masayoshi Shinmei, 4-4, Nakaaral 4-chome, Tokorozawa-shi, Saitama-ken, 359; Taro Hayakawa, 406, Mukaigaoka 3-chome, Tenpaku-ku, Nagoya-shi, Aichi-ken, 468; Kazushi Iwata, 190 Ikarihigashimachi, Takaoka-shi, Toyama-ken, 933; Yumi Korin, Fu-134, Takamatsucho, Kahoku-gun, Ishikawa-ken, 929-12; Shuji Kodama, 603, Takaokasukaihaitsu, 1868, Nagae, Takaoka-shi, Toyama-ken, 933; Shinichi Yoshida, 13-16, Nakajima 4-chome, Toyama-shi, Toyama-ken, 930, all of Japan

[21] Appl. No.: 417,847

[22] Filed: Apr. 6, 1995

Related U.S. Application Data

[63] Continuation of Ser. No. 923,980, Sep. 17, 1992, abandoned.

[30] Foreign Application Priority Data

Jan. 21, 1991 [JP] Japan ..................................... 3-078155
Jan. 21, 1992 [WO] WIPO ....................... PCT/JP92/00041

[51] Int. Cl.$^6$ ...................... G01N 33/573; G01N 33/543; G01N 33/564
[52] U.S. Cl. ........................... 435/7.4; 435/7.94; 435/23; 435/70.21; 435/172.2; 435/240.27; 436/506; 436/524; 436/528; 436/531; 436/534; 436/538; 436/548; 436/512; 530/388.26; 935/100; 935/104; 935/106; 935/110
[58] Field of Search ..................................... 435/7.4, 7.94, 435/70.21, 172.2, 240.27, 23; 436/524, 528, 531, 534, 538, 548, 506, 512; 530/388.26; 935/100, 104, 106, 110

[56] References Cited

U.S. PATENT DOCUMENTS 4,376,110  3/1983  David et al. ............................ 435/7.23
4,859,595  8/1989  Strosberg et al. ................... 435/172.2

OTHER PUBLICATIONS

Journal of Biological Chemistry—vol. 265, No. 18, (1990) J,K, MacNaul et al, pp. 17238–17245.
American Journal of Pathology, vol. 135, No. 6, (1989), J.P. Case et al, pp. 1055–1064.
Nature—vol. 256, (1975), G. Kohler et al, pp. 495–497.
Fujimoto et al, 1994, Enzyme Immunoassays for Matrix Metalloproteinases and Their Inhibitors. Connective Tissue 26:240–241.
Okada et al, 1988. The precursor of a metalloendopeptidase from human rheumatoid synovial fibroblasts. Biochem J. 254:731–41.
Obata et al, 1992, A one–step sandwich enzyme immunoassay for human matrix metalloproteinase–3 (stronelypsin–1) Using Monoclonal Antibodies: Clinica Chimica Acta 211:59–72.
Rehfeld et al, 1983. Residue–specific radioimmunoanalysis: a novel analytical tool. Application to the C–terminus of CCK/gastrin peptides J. Biochem Biophys. Meth 7:161–170.
Cooksley et al, 1990. Immnoassays for the Detection of Human . . . Stromalysis . . . Matrix 10:285–91.
Walakovits et al, Jan 1992. Detection of Stromelysin and Collagenase in Synovial Fluid From Patients With Rheumatoid Arthritis and Posttraumatic Knee Injury. Arthritis and Rheumatism 35:35–42.
Whitman et al, 1986. Comparison of Human Stromalysin and Collagenase by Cloning and Sequence Analysis. Biochem J 240:913–16.
Hellstrom et al, 1985. In: *Monoclonal Antibodies for Cancer Detection and Therapy* (Baldwin et al, eds.) p. 20.

*Primary Examiner*—Paula K. Hutzell
*Assistant Examiner*—James L. Grun

[57] ABSTRACT

Anti-human stromelysin monoclonal antibodies reactive with latent and active forms of stromelysin without discrimination between the two, each being immunoreactive with only one of the antigenic determinants of human stromelysin, are provided. The use of a combination of two such monoclonal antibodies which specifically react with different antigenic determinants of human stromelysin renders it possible to accurately determine the amount of human stromelysin in human body fluids, and thus to carry out the diagnosis of rheumatoid arthritis.

There are thus provided said monoclonal antibodies per se, a sandwich enzyme immunoassay for the determination of the amount of human stromelysin in human body fluid samples using a combination of two such monoclonal antibodies, and a method for the diagnosis of rheumatoid arthritis using said immunoassay.

9 Claims, 1 Drawing Sheet

ANTI-HUMAN STROMELYSIN MONOCLONAL ANTIBODY AND METHOD FOR DIAGNOSIS OF RHEUMATOID ARTHRITIS BY ENZYME IMMUNOASSAY

This application is a continuation, continuation-in-part, of application Ser. No. 07/923,980 filed on Sept. 17, 1992, now abandoned.

FIELD OF THE INVENTION

The present invention relates to anti-human stromelysin monoclonal antibodies, an enzyme immunoassay using such monoclonal antibodies, and a method for the diagnosis of rheumatoid arthritis by determination, on the basis of said immunoassay, of the amount of human stromelysin present in samples as the sum of the amount of latent stromelysin and that of active stromelysin.

BACKGROUND ART

Stromelysin, also called proteoglycanase or MMP-3 (matrix metalloproteinase-3), is a substance produced in fibroblasts or tumor cells stimulated by different cytokines, growth factors, etc. In the live body, it is present in blood or synovial fluids, besides being produced locally in joints of patients with rheumatoid arthritis.

Stromelysin has been considered to play an important role in the intraarticular cartilage destruction in patients with rheumatoid arthritis since it decomposes gelatin, laminin, type IV collagen, fibronectin etc. in addition to proteoglycan and type IX collagen, both being important extracellular matrices for articular cartilage.

Stromelysin is produced in the latent form, also called prostromelysin, which is converted, by activation in the extracellular matrix, into active stromelysin. The latent stromelysin, when treated with serine proteases such as plasmin or trypsin, undergoes restricted decomposition into active stromelysin. The active stromelysin also forms when the latent stromelysin is treated with 4-aminophenylmercuric acetate (APMA). The latent stromelysin has a molecular weight (Mr) of either 57,000 daltons (57 kD) or 59,000 (59 kD), the 59 kD stromelysin being a glycosylated form of the 57 kD stromelysin.

Furthermore, the active stromelysin resulting from the protease digestion shows an Mr of 45 kD. The active stromelysin obtained by the APMA treatment shows an Mr of 45 kD and 46 kD, while a less active stromelysin with an Mr of 28 kD is obtained by extending the APMA treatment duration to 12 hours or more.

For the diagnosis of rheumatoid arthritis there have heretofore been used Rose's method based on the detection of rheumatoid factor, modified Rose's method by Heller, the RAHA-test, the RA-test, etc. These methods, however, possess such disadvantage that blood rheumatoid factor is not specific to patients with rheumatoid arthritis and that rheumatoid factor assay kits based on such methods are poor in accuracy or reproducibility.

Assays for erythrocyte sedimentation rate (ESR) or C-reactive protein (CRP), although rendering it possible to determine the activity of the above mentioned disease, are not suitable for the diagnosis thereof. With the detection of anti-nuclear antibodies or LE cells, it is difficult to conduct accurate diagnosis of rheumatoid arthritis because it is poor in specificity to the disease and also because such antibodies or cells are frequently detectable in other collagen diseases. There also exist methods of determining hyaluronic acid, but they are inconvenient in that only synovial fluids are usable as samples.

Human stromelysin has been found to be synthesized and secreted in large quantities locally in joints of patients with rheumatoid arthritis among other arthropathies. Stromelysin is also synthesized and secreted in synovial lining cells or joint chondrocytes of patients with osteoarthritis. However, since polyarthritis is produced in rheumatoid arthritis whereas monoarthritis is generally produced in osteoarthritis, blood or synovial fluids of patients with osteoarthritis show no significant increase in the amount of stromelysin as compared with normal subjects.

The present invention is of particular significance with respect to the diagnosis of rheumatoid arthritis, since no biochemical marker has been found so far that could serve as an indicator of articular destruction, as mentioned above.

DISCLOSURE OF THE INVENTION

Figure 1:
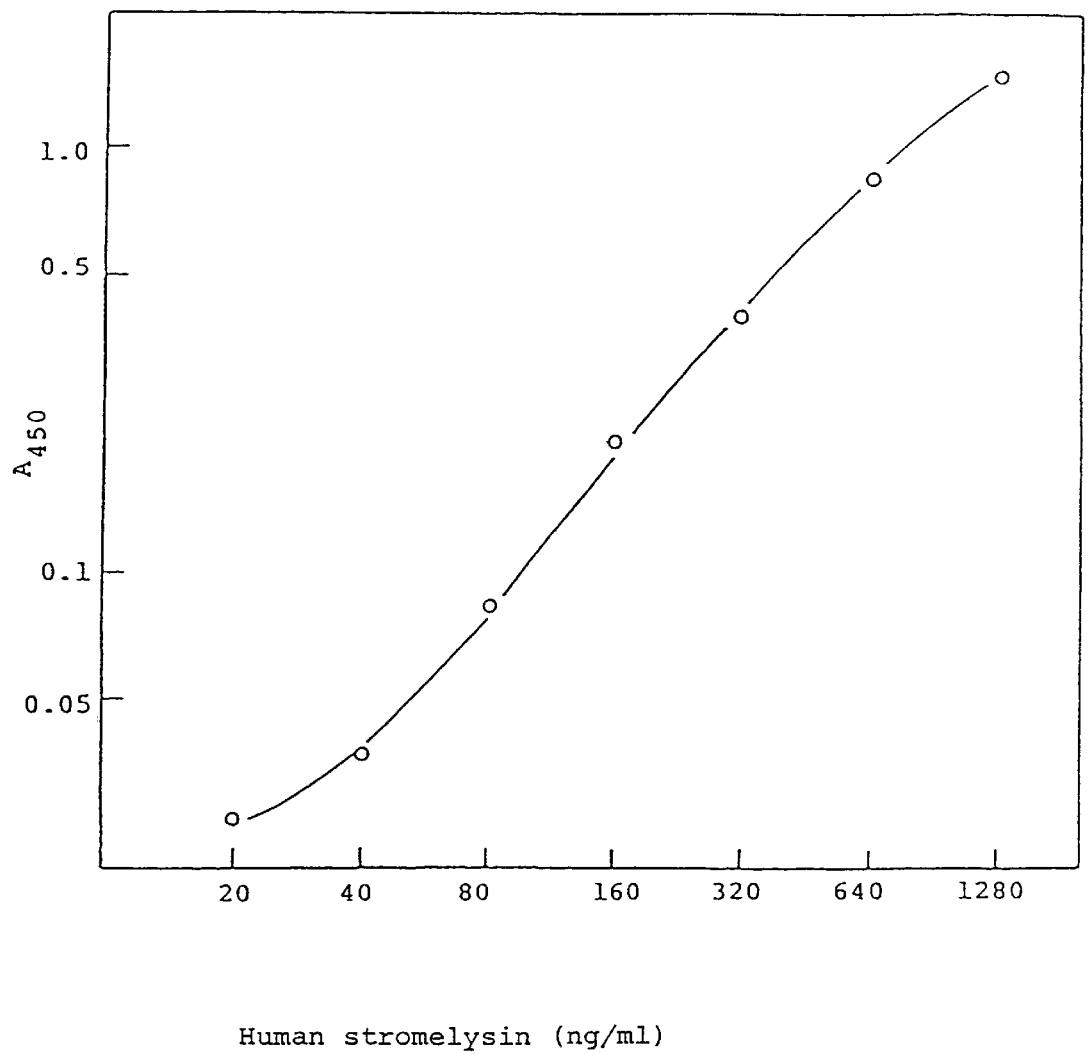
FIG. 1 shows the standard curve obtained in Example 3(c), i.e., the standard curve for human stromelysin prepared by way of the one-step sandwich method with IgG (clone 55-3G3) as the solid phase antibody and IgG (clone 55-2A4) as the labeled antibody.

The present invention provides IgG-class anti-human stromelysin monoclonal antibodies and a method for the preparation thereof by way of the use of hybridomas, as well as an enzyme immunoassay for human stromelysin based on the sandwich method using said monoclonal antibodies, and a method for the diagnosis of rheumatoid arthritis which comprises using said immunoassay to measure the amount of stromelysin in blood or other samples from patients with rheumatoid arthritis and comparing the measured amount with the amount of stromelysin in the corresponding samples from normal subjects.

Thus, according to the present invention, there are provided:

(1) Monoclonal antibodies reactive with latent stromelysin (prostromelysin) and active stromelysin without discrimination between the two, each being a monoclonal antibody having immunoreactivity with only one of the antigenic determinants of human stromelysin;

(2) An enzyme immunoassay for human stromelysin characterized in that the sum of the amount of latent stromelysin (prostromelysin) and that of active stromelysin is determined by the sandwich method using a combination of two monoclonal antibodies which specifically bind to their respective different antigenic determinants of human stromelysin; and (3) A method for the diagnosis of rheumatoid arthritis comprising measuring, by way of said enzyme immunoassay, the amount of human stromelysin present in a sample as the sum of the amount of latent stromelysin and that of active stromelysin and comparing the measured amount with that of corresponding samples from normal subjects.

The above mentioned enzyme immunoassay employed in the present invention will be understood from examples which will be given below. They may be selected, for example, from any conventional enzyme immunoassays of different types: competitive methods such as the solid phase antibody method, double antibody method, EMIT (enzyme multiplied immunoassay technique), enzyme channeling immunoassay, enzymatic activity modifier immunoassay and liposome membrane-enzyme immunoassay, and non-competitive methods such as sandwich method, immunoenzyme metric assay, enzymatic activity enhanced immunoassay and proximal linkage immunoassay.

In the above mentioned immunoassay, a variety of materials in any appropriate usage forms which effective passively adsorb antigens or antibodies may be chosen for use as solid supports, e.g. polystyrenes, polycarbonates, polypropylenes or polyvinyls in such forms as spheres, microplates, sticks or test tubes.

As labeling enzymes there may be used, for example, peroxidase, alkaline phosphatase and β-D-galactosidase. As means for determining their enzymatic activity there may be used, for example, colorimetry, fluorometry, bioluminescence method or chemiluminescence methods. Assays may be carried out as appropriate by using any combination of these enzymes and means for determining their enzymatic activity.

As the antibody to be labeled with an enzyme, there may be used an IgG fraction obtainable by the fractionation of a material containing antibodies with ammonium sulfate, followed by purification on an anion exchange gel such as DEAE-Sephacel, as well as Fab' that specifically reacts with antigen molecules and that is obtainable by digestion with pepsin followed by reduction.

Monoclonal antibodies according to the present invention, a method for the preparation thereof, an enzyme immunoassay for human stromelysin using said monoclonal antibodies, and a method for the diagnosis of rheumatoid arthritis using said immunoassay will now be illustrated in more detail by way of the following examples, but it is to be understood that this invention is not limited thereto.

EXAMPLE 1

Preparation of Monoclonal Antibodies against Human Stromelysin (a) Preparation of antigen-human prostromelysin In accordance with the procedure described by the present inventors in Okada et al. (1988) Biochem. J. 254:731–741, synovial cells from a patient with rheumatoid arthritis were cultivated in Dulbnecco-modified Eagle's medium (supplied by Nissui Seiyaku). Thus, synovial tissue from a patient with rheumatoid arthritis who underwent arthroplasty was minced before synovial cells were liberated therefrom enzymologically according to the method of Dayer et al. (1976) Proc. Natl. Acad. Sci. USA 73:945–949. The cells were then cultivated in Dulbecco-modified Eagle's medium containing 20% fetal bovine serum, penicillin and streptomycin.

The resultant cells from the primary culture in accordance with the procedure described in the literature cited above were further cultivated in rabbit alveolar-macrophage-conditioned medium in serum-free medium as described by Okada et al. (1986) J. Biol. Chem. 261:14245–14255, recovering the culture on the 5th-7th day. The thus obtained culture medium was processed.

All purification procedures were carried out at 4° C. with buffer containing 10Mm $Ca^{2+}$, 0.05% Brij 35 and 0.02% $NaN_3$ unless otherwise stated. The activity of prostromelysin was measured against [$^3$H]Cm-Tf (reduced carboxymethylated transferrin) after activation with 1.5 mM $NH_2PhHgAc$.

When subjected to sodium dodecyl sulfate-polyacrylamide gel electrophoresis (SDS-PAGE), the resultant purified human stromelysin showed a single band having a Mr about 57 kD. This purified human stromelysin is a latent form, i.e., prostromelysin. This product does not contain the 59 kD glycosylated prostromelysin because a concanavalin A Sepharose column was used to obtain the product in the procedure mentioned above.

(b) Preparation of antibody-producing cells

Two 6-week-old female Balb/c mice were initially immunized intraperitoneally with 15 μg in 0.2 ml emulsion of purified human prostromelysin described above in (a) in Freund's complete adjuvant. The mice then received, after 17 days, a booster injection of 15 μg of the human prostromelysin dissolved in 10 mM Tris-HCl buffer (pH 7.5). As the final immunization, the mice received, after 54 days, an additional booster injection by intravenous administration of 16.5 μg/mouse of the antigen dissolved in 10 mM Tris-HCl buffer (pH 7.5). On the 3rd day after the final immunization the spleen was extirpated and the splenocytes were prepared.

(c) Cell fusion (1) Materials and methods used are as follows

RPMI 1640 culture medium: RPMI No. 1640 (Flow Lab.) supplemented with sodium bicarbonate (24 mM), sodium pyruvate (1 mM), penicillin G potassium (50 U/ml), streptomycin sulfate (50 μg/ml) and amikacin sulfate (100 μg/ml), adjusted to pH 7.2 with dry ice and filtered through a 0.2 μm Toyo membrane filter for sterilization.

NS-1 culture medium: the above RPMI 1640 culture medium supplemented with 15% (v/v) filter-sterilized fetal bovine serum (M.A. Bioproducts).

PEG 4,000 solution: Serum-free RPMI 1640 culture medium, containing 50% (w/w) polyethylene glycol 4,000 (PEG 4,000, Merck & Co., Inc.).

Utilizing an 8-azaguanine-resistant myeloma cell line, SP-2 (SP-2/0·Ag14), cell fusion was effected according to method of Oi et al. described in "Selected Methods in Cellular Immunology" (eds. B. B. Mishell and S. M. Shiigi, W. H. Freeman and Company, (1980), pp. 351–372).

(2) The karyo-splenocytes prepared as described in (b) (cell viability 100%) were fused in a ratio of 5 to 1 with myeloma cells (cell viability 100%). Thus, the splenocytes and the myeloma cells were separately washed in RPMI 1640 culture medium, then suspended in the same medium and mixed together for fusion in the ratio described above. 37 ml of the RPMI 1640 culture medium were put into a 50 ml conical styrene resin test tube (Sumitomo Bakelite), and centrifuged at 1,000 rpm for 10 min., and the supernatant was completely removed by suction. To the precipitated cells was added dropwise over 1 min. 4.5 ml of the PEG 4,000 solution warmed at 37° C. with gentle stirring. The cells were resuspended and dispersed by stirring for another minute. To the suspension was then added dropwise over 1 min. 4.5 ml of RPMI 1640 culture medium warmed at 37° C.

After repeating the same operation once more, the cells were dispersed, by adding 31.7 ml of the same culture medium dropwise over 2 to 3 min. under continuous agitation. The dispersion was centrifuged at 1,000 rpm for 7 min., and the supernatant was completely discarded by suction. To the precipitated cells was added rapidly 45 ml of NS-1 culture medium warmed at 37° C., and big cell clumps were then dispersed carefully with a 10 ml pipette.

The dispersion was diluted by adding the same into a bottle containing 91 ml of the same culture medium, and distributed into a 96-well microwell made of polystyrene (Iwaki Glass) so that 6.0×105 cells/0.1 ml were present in each well. The microwells were incubated at 37° C. in 7% $CO_2$/93% air under 100% humidity.

(d) Selective proliferation of hybridomas with the aid of a selective culture medium:

(1) Culture media used are as follows:

HAT selection medium: the NS-1 culture medium mentioned above in (c) supplemented with hypoxanthine (100 μM), aminopterin (0.4 μM) and thymidine (16 μM).

HT culture medium: the same composition as the HAT medium mentioned above except that aminopterin is not present.

(2) One day after the cultivation mentioned above in (c) was started (i.e., on the first day), two drops (ca. 0.1 ml) of HAT culture medium were added with a pipette. On the 2nd, 3rd, 5th and 8th days, half (0.1 ml) of each culture medium was replaced with fresh HAT culture medium. On the 10th day, half of each culture medium was replaced with fresh HT culture medium, whereupon sufficient growth of hybridomas was observed. All the wells containing hybridomas grown were tested to see if there were positive wells, using a solid phase-antibody binding test (ELISA) as will be described in (e).

All the cultures with hybridomas positive in the test above were transferred to a 24-well cell well made of polystyrene (Sumitomo Bakelite) containing 1 ml of the HT culture medium containing $10^7$ mouse thymocytes as feeders. The cultures were subjected to cultivation, as described in (c), at 37° C. in 7% $CO_2$ for five days. At the time sufficient growth of hybridomas was observed, the cultures were checked again by the ELISA method, and subjected to a cloning procedure by limiting dilution as will be explained in (f) below. The residual culture after cloning was transferred into a 25 $cm^2$ tissue culture flask made of polystyrene (Iwaki Glass), for the preparation of a frozen sample for storage.

(e) Screening for hybridomas capable of producing Anti-human stromelysin antibody by means of the solid phase-antibody binding test (ELISA):

The method used for the present example was based on the method of Rennard et al. described in Anal. Biochem., 104, 205–214, (1980), which is appropriate for the detection of antibody production in hybridomas. Each well of a 96-well microtitration plate (Flow Lab.) was coated with 30 ng/well of human stromelysin. To the wells was added a part of the supernatant from the wells containing hybridomas grown as obtained in (d) above. The incubation was carried out at room temperature for about 1 hr. After the addition of goat anti-mouse immunoglobulin (Cappel Lab.) labeled with peroxidase as a secondary antibody, further incubation was carried out at room temperature for about 1 hr. After the addition of $H_2O_2$ and o-phenylenediamine as substrate, the measurement of the absorbance at 492 nm was carried out using a microplate reader (MRP-A4, Toyo Soda).

(f) Cloning:

In order to obtain hybridomas capable of producing monoclonal antibodies it is necessary, after the procedure mentioned above in (d), for cloning to be carried out according to the limiting dilution method, since each well can develop two or more kinds of hybridomas. A cloning culture medium containing in NS-1 culture medium $10^7$ cells per ml of mouse thymocytes as feeders was prepared. 5, 1 and 0.5/well of hybridomas were added to 36, 36 and 24 wells of a 96-well microwell, respectively.

About 0.1 ml of NS-1 culture medium was further added to each well on the 5th day. On the 10th day, half (0.1 ml) of each culture medium was replaced with fresh NS-1 culture medium. About 14 days after the cloning, sufficient growth of hybridoma could be recognized, and the hybridomas were subjected to ELISA. When not all of the tested wells were shown to be positive, the colonies in antibody-positive wells were enumerated and out of them one well exhibiting the formation of one single colony was selected for recloning. Finally, 14 hybridoma clones capable of producing monoclonal antibodies to human stromelysin were obtained.

(g) Mass production of monoclonal antibody using hybridomas

Hybridomas were proliferated in a conventional manner. Thus, monoclonal antibodies can be obtained in a concentration of 10–100 µg/ml from the supernatant of an appropriate culture medium such as NS-1 culture medium in which each of the resultant hybridomas was subjected to cultivation. If a large amount of antibody is to be produced, on the other hand, a carcinogenic excitant, Pristane (2,6,10, 14-tetramethylpentadecane, Aldrich Chem.), was administered to animals (Balb/c mice) intraperitoneally in a volume of 0.5 ml per animal, which animals were of the syngenic strain as those providing the splenocytes and the myeloma cells.

One to 3 weeks after the administration, $1 \times 10^7$ cells of each hybridoma were administered intraperitoneally as above, and ascites containing 4–7 mg/ml of monoclonal antibody were obtained after 1 to 2 weeks.

(h) Isotypes of monoclonal antibodies

In accordance with the above-described ELISA method, the culture supernatant for each monoclonal antibody-producing hybridoma was added to a microtitration plate coated with human stromelysin. After washing with 0.05% Tween 20-containing PBS, isotype-specific rabbit anti-mouse Ig antibodies (Zymed Lab.) were added thereto. After washing with PBS, goat anti-rabbit IgG (H+L) antibody labeled with peroxidase was added thereto, and 2,2'-azino-di(3-ethylbenzthiazoline sulfonic acid) and hydrogen peroxide as substrate were then added for detection.

The results are shown collectively in Table 1, below. Out of the resultant monoclonal antibodies against human stromelysin, ten antibodies were found to contain immunoglobulin chain γ 1/κ, two antibodies γ2a/κ, and two antibodies γ 2b/κ. The results of reactivity with human stromelysin were obtained in accordance with the procedure described below in (j).

(i) Purification of monoclonal antibody

Each of the ascites obtained in (g) was purified by using an Affi-Gel Protein A MAPS-II kit (Bio-Rad).

(j) Reactivity of human stromelysin with monoclonal antibodies

As described by the present inventors et al. in Biochem. J. 254, 731–741 (1988), the conditioned medium of human synovial cells contain latent stromelysin with an Mr 59 kD and 57 kD. If, however, the culture is treated with 4-aminophenyl mercuric acetate (APMA) in the presence of $Ca^{2+}$, the latent stromelysins are activated into active stromelysin with an Mr 46 kD and 45 kD. Accordingly, the above-mentioned conditioned medium containing the latent stromelysins and the APMA-treated conditioned medium containing the active stromelysins were subjected to SDS-PAGE.

In accordance with the method of Tanabe as described in "Saibo Kogaku" (Cell Technology) 1 & 2, 1061–1068 (1983), Western blotting was carried out, using peroxidase-labeled goat anti-mouse immunoglobulin, to study the reactivity of each monoclonal antibody obtained in Example 1 (i) with the latent stromelysins (59 kD and 57 kD) and with the active stromelysins (59 kD and 57 kD).

The results are shown in Table 1. As shown in Table 1, all fourteen monoclonal antibodies were found to react with all the latent and active forms of stromelysin. Although latent collagenase or latent gelatinase are also present in the conditioned medium, only bands of 60 kD and 57 kD that correspond to the molecular weights of stromelysin were observed on the Western blotting patterns mentioned above, and no bands of 55 kD, and 52 kD corresponding to the molecular weights of collagenase, or 72 kD, corresponding to the molecular weight of gelatinase, were detected. The above-mentioned fourteen monoclonal antibodies were thus confirmed to react specifically with stromelysin but not with collagenase or gelatinase.

Example 2

Immunohistologic staining using anti-human stromelysin monoclonal antibody

Human stromelysin, after being produced inside a cell, is continuously secreted into the exterior of the cell without being stored in the cell. Accordingly, in order to identify the cells where human stromelysin is produced, synovial tissue from a patient with rheumatoid arthritis was cultivated for 3 hrs in the presence of monensin (2 μM) to accumulate human stromelysin in cells producing it.

The resultant tissue was fixed with periodate-lysine-paraformaldehyde before paraffin sections were prepared. These sections were deparaffinized and endogenous peroxidase therein was blocked with hydrogen peroxide. The sections were reacted with the anti-human stromelysin monoclonal antibodies (IgG) obtained in Example 1 (i). After being washed well with PBS, the sections were reacted with biotinylated horse anti-mouse IgG (H+L) and then with avidin-biotin-peroxidase complex (Vector Lab.).

The thus obtained sections were washed with PBS, and diaminobenzidine and hydrogen peroxide were used as substrates for color development. In the immunohistologic staining where IgG (clone 55-2A4) and IgG (clone 55-3G3) were used as anti-human stromelysin monoclonal antibodies, synovial lining cells from patients with rheumatoid arthritis were stained positive, in either case, with respect to human stromelysin. It has thus been found that both clone 55-2A4 and clone 55-3G3 are usable for immunohistologic staining.

The above mentioned hybridomas clones 55-2A4 and 55-3G3 have been deposited with the Fermentation Research Institute Agency of Industrial Science and Technology under accession numbers Bikoken Kinki No. 12303 (FERM BP-3743) and Bikoken Kinki No. 12304 (FERM BP-3744), respectively.

Example 3

Quantitative method for detecting human stromelysin
(a) Preparation of enzyme-labeled monoclonal antibodies
(1) Preparation of Fab' fraction Each purified monoclonal antibody (IgG) obtained in Example 1(i) was dissolved in a 0.1M acetate buffer solution (pH 4.2) and the solution was digested with pepsin as follows. Pepsin was added to the fraction to 2% (w/w) based on the IgG, and the mixture was subjected to digestion at 37° C. for 24 hrs.

The digested product was adjusted to a pH of 7.0 with a 2M Tris solution to stop the reaction.

The product was gel-filtrated on an Ultrogel AcA 44 column equilibrated with a 0.1M phosphate buffer solution (pH 7.0) to obtain the F (ab')2 fraction.

The F (ab')$_2$ fraction was then dialyzed against a 0.1M phosphate buffer solution (pH 6.0) containing 5mM ethylenediamine tetraacetic acid (EDTA), and aminoethanethiol was added to a final concentration of 10 mM to effect reduction at 37° C. for 90 min. The product was gel-filtrated on an Ultrogel AcA 44 column equilibrated with a 0.1M phosphate buffer solution (pH 6.0) containing 5mM EDTA to obtain the Fab' fraction.
(2) Preparation of maleimide-labeled peroxidase fraction Separately from the procedure described in (1) above, peroxidase was labeled with a maleimide compound as follows. Peroxidase was dissolved in a 0.1M phosphate buffer solution (pH 7.0) to 10 mg/ml and to the solution was added 25 moles, per mole of peroxidase, of N-(ε-maleimidocaproyloxy) succinimide as a solution in dimethylformamide (DMF) for reaction at 30° C. for 30 min. The product was gel-filtrated on a Sephadex G-50 column equilibrated with a 0.1M phosphate buffer solution (pH 6.0) to obtain the maleimide-labeled peroxidase fraction.
(3) Preparation of the Fab'-peroxidase conjugate fraction The fractions as prepared in (1) and (2) above were admixed so that equimolar amounts of Fab' and maleimide-labeled peroxidase in the respective fractions were mixed. The mixture was then diluted with a 0.1M phosphate buffer solution (pH 6.0) containing 5mM EDTA to a final concentration, with respect to both Fab' and maleimide-labeled peroxidase, of 100μM.

After reaction at 4° C. for 20 hrs. was added 10 moles per mole of Fab' of N-ethylmaleimide were added to block unreacted thiol groups. The product was gel-filtrated on an Ultrogel AcA 44 column equilibrated with a 0.1M phosphate buffer solution (pH 6.5) to obtain Fab'-peroxidase conjugate fraction, to which 0.1% bovine serum albumin (BSA) and 0.001% chlorhexidine were added for storage at 4° C.
(b) Preparation of monoclonal antibody-coated spheres:

According to the method of Ishikawa et al. as described in J. Immunoassay 4, 209–327 (1983), purified monoclonal antibody obtained in Example 1(i) was dissolved in a 0.1M phosphate buffer solution (pH 7.5) containing 0.1% sodium azide to a concentration of 100 μg/ml.

Polystyrene spheres (6.5 mm in diameter, supplied by Precision Plastic Ball) were soaked therein and allowed to stand at 4° C. for 24 hrs. After removal of the monoclonal antibody solution, the spheres were washed with a 10 mM phosphate buffer solution (pH 7.0) containing 0.1% BSA, 0.1% NaCl and 0.001% chlorhexidine and stored at 4° C.
(c) Enzyme Immunoassay To prepare standard samples, the purified human prostromelysin obtained in Example 1(a) was dissolved in a 10mM phosphate buffer solution (pH 7.0) containing 0.1M sodium chloride and 1% BSA to prepare a 1280 ng/ml solution. The solution was subjected to serial dilution and a 50 μl portion was taken from each dilution.

On the other hand, a 50 μl aliquot of serum from normal subjects, patients with rheumatoid arthritis (RA) and patients with osteoarthritis (OA) were used as test samples.

Each of the samples mentioned above was placed in a test tube and dissolved in 300 μl of a 30mM phosphate buffer solution (pH 7.0) containing the Fab'-peroxidase conjugate fraction (100 ng/ml) prepared in (a) above, 0.1M sodium chloride and 10mM EDTA. One monoclonal antibody-coated polystyrene sphere prepared as described above was added to each of these test tubes and the mixture was allowed to stand at room temperature for one hr and then washed with a 5mM phosphate buffer solution (pH 7.0) containing 50mM sodium chloride.

A 300 μl portion of 0.025% tetramethylbenzidine (substrate for peroxidase) dissolved in a 0.1M acetate buffer solution (pH 5.5) containing 9% DMF, and then a 300 μl portion of 0.0075% acqueous hydrogen peroxide, were added, and after the mixtures were allowed to stand at room temperature for 30 min., a 1400 μl portion of 1.75N sulfuric acid were added to stop the reaction. The absorbance at 450 nm of the liquid reaction mixtures was measured using a Shimazu Micro-Flow spectrophotometer (UV-730), and the concentration of human stromelysin corresponding to the absorbance of the test sample was read from a standard curve prepared with the standard samples.

The standard curve is shown in FIG. 1, which was obtained when IgG (clone 55-3G3) was used as the solid phase antibody and IgG (clone 55-2A4) was used as the labeled antibody. Quantitation of human stromelysin is possible also with other monoclonal antibody combinations, but the highest sensitivity was obtained with the above mentioned combination. Furthermore, as shown in Table 1, the resultant monoclonal antibodies are able to react with both latent and active forms of stromelysin. In the above described sandwich assay systems, therefore, both latent and active forms of stromelysin in samples are quantitated simultaneously.

On the other hand, since neither the solid phase antibody nor the labeled antibody reacts with collagenase or gelatinase as described in Example 1 (j), only stromelysin is specifically quantitated in the above described assay systems. As shown in FIG. 1, $A_{450}$ increases as the concentration of human stromelysin in standard samples increases, with the determination sensitivity being 20 ng per ml of sample.

(d) Quantitation of stromelysin in patients with RA or OA

In accordance with the enzyme immunoassay described in (c) above, stromelysin in bloods from normal subjects, patients with RA and patients with OA was quantitated. A 50 μl aliquot of serum samples from normal subjects (9 samples), patients with RA (10 samples) and patients with OA (11 samples) were used to measure the concentration of stromelysin therein. The results are as shown in Table 2. The concentration of stromelysin (mean ± S.D.) in sera from normal subjects was 65.9±20.3 ng/ml. On the other hand, the concentration of stromelysin (mean ± S.D.) in sera from patients with RA was 731.8±369.4 ng/ml, significantly higher than that in sera from normal subjects, whereas the concentration of stromelysin in sera from patients with OA was 84.3±49.6 ng/ml, not significantly different from that in sera from normal subjects.

As samples for carrying out the diagnosis as described above, there may be used bloods or synovial fluids, or where appropriate, stromelysin-containing samples available from a live body.

Furthermore, stromelysin in synovial fluids from patients with RA and with OA was measured. The concentration of stromelysin was measured in synovial samples from patients with RA (9 samples) and with OA (10 samples). When of synovial fluids of each of 50 μl were used, the absorbance ($A_{450}$) exceeded the range readable from the standard curve, so that the synovial fluids were diluted 10–100 times before being subjected to the measurement.

The results were as shown in Table 3. Thus, the concentration of stromelysin (mean ± S.D.) in synovial fluids from patients with RA was 49257±23267 ng/ml, significantly higher than that for patients with OA (10097±640 ng/ml).

TABLE 1

| Clone No. | Subclass | Reactivity with Latent Stromelysin | Reactivity with Active Stromelysin |
| --- | --- | --- | --- |
| 55-1F5 | IgG1/κ | + | + |
| 55-2A4 | IgG1/κ | + | + |
| 55-3G3 | IgG1/κ | + | + |
| 55-6F10 | IgG2a/κ | + | + |
| 55-7C10 | IgG2b/κ | + | + |
| 55-8A3 | IgG2a/κ | + | + |
| 55-9A9 | IgG1/κ | + | + |
| 55-10H2 | IgG1/κ | + | + |
| 55-11F1 | IgG2b/κ | + | + |

TABLE 1-continued

| Clone No. | Subclass | Reactivity with Latent Stromelysin | Reactivity with Active Stromelysin |
| --- | --- | --- | --- |
| 55-14G6 | IgG1/κ | + | + |
| 55-16D5 | IgG1/κ | + | + |
| 55-18D2 | IgG1/κ | + | + |
| 55-19D5 | IgG1/κ | + | + |
| 55-20A2 | IgG1/κ | + | + |

TABLE 2

| Sera from normal subjects | | Sera from patients with RA | | Sera from patients with OA | |
| --- | --- | --- | --- | --- | --- |
| Sample No. | Concentration of Stromelysin (ng/ml) | Sample No. | Concentration of Stromelysin (ng/ml) | Sample No. | Concentration of Stromelysin (ng/ml) |
| 1 | 42 | 1 | 470 | 1 | 170 |
| 2 | 66 | 2 | 650 | 2 | 81 |
| 3 | 53 | 3 | 1500 | 3 | 20 |
| 4 | 66 | 4 | 790 | 4 | 34 |
| 5 | 42 | 5 | 118 | 8 | 75 |
| 6 | 64 | 6 | 500 | 6 | 113 |
| 7 | 68 | 7 | 570 | 7 | 156 |
| 8 | 87 | 8 | 960 | 8 | 70 |
| 9 | 105 | 9 | 940 | 9 | 98 |
| | | 10 | 820 | 10 | 20 |
| | | | | 11 | 90 |
| Mean | 65.9 | Mean | 731.8 | Mean | 84.3 |
| S.D. | 20.3 | S.D. | 369.4 | S.D. | 49.6 |

TABLE 3

| Synovial fluids from patients with RA | | Synovial fluids from patients with OA | |
| --- | --- | --- | --- |
| Sample No. | Concentration of Stromelysin (ng/ml) | Sample No. | Concentration of Stromelysin (ng/ml) |
| 1 | 22050 | 1 | 2478 |
| 2 | 58800 | 2 | 19320 |
| 3 | 69300 | 3 | 6405 |
| 4 | 79800 | 4 | 5040 |
| 5 | 4200 | 5 | 10080 |
| 6 | 56280 | 6 | 21000 |
| 7 | 46200 | 7 | 13440 |
| 8 | 57960 | 8 | 11760 |
| 9 | 48724 | 9 | 8505 |
| | | 10 | 2940 |
| Mean | 49257 | Mean | 10097 |
| S.D. | 23267 | S.D. | 6402 |

We claim:

1. A monoclonal antibody which specifically binds to latent stromelysin (prostromelysin) and active stromelysin without discrimination between the two, but which does not bind to either collagenase or gelatinase, wherein said monoclonal antibody is produced by a hybridoma which is selected from the group consisting of hybridoma 55-2A4, FERM BP-3743, and hybridoma 55-3G3, FERM BP-3744.

2. The monoclonal antibody according to claim 1, wherein said hybridoma is hybridoma 55-2A4, FERM BP-3743.

3. The monoclonal antibody according to claim 1, wherein said hybridoma is hybridoma 55-3G3, FERM BP-3744.

4. A sandwich enzyme immunoassay for determining the amount of active stromelysin or prostromelysin in a sample selected from the group consisting of blood, serum and synovial fluid, comprising the steps of:

(a) contacting the sample suspected of containing active stromelysin or prostromelysin with an enzyme-labeled monoclonal antibody or Fab' fraction thereof, wherein said monoclonal antibody or Fab' fraction thereof specifically binds to a first region of active stromelysin or prostromelysin without discrimination between the two, but does not bind to either collagenase or gelatinase, to form complexes of said active stromelysin or said prostromelysin and said monoclonal antibody or said Fab' fraction thereof;

(b) contacting said complexes of step (a) with an immobilized monoclonal antibody which specifically binds to a second region of said active stromelysin or prostromelysin without discrimination between the two, and which also does not bind to either collagenase or gelatinase, so as to form immobilized complexes of said enzyme-labeled monoclonal antibody or Fab' fraction thereof, said active stromelysin and/or said prostromelysin, and said immobilized monoclonal antibody;

(c) washing said complexes of step (b);

(d) incubating said complexes of step (c) with a substrate of said enzyme to from an amount of end product;

(e) determining the amount of end product formed in step (d); and (f) relating said amount of end product determined in step (e) as indicative of the amount of active stromelysin and prostromelysin in said sample by referring to a standard curve for prostromelysin, wherein said enzyme-labeled monoclonal antibody is a monoclonal antibody produced by hybridoma 55-2A4, FERM BP-3743, and wherein said immobilized monoclonal antibody is a monoclonal antibody produced by hybridoma 55-3G3, FERM BP-3744.

5. The sandwich enzyme immunoassay of claim 4, wherein said immobilized monoclonal antibody is immobilized on a solid support selected from the group consisting of a sphere, a microplate, a stick, and a test tube.

6. The sandwich enzyme immunoassay of claim 5, wherein said solid support is made of a material selected from the group consisting of a polystyrene, a polycarbonate, a polypropylene, and a polyvinyl.

7. The sandwich enzyme immunoassay of claim 4, wherein said enzyme-labeled monoclonal antibody or Fab' fraction thereof is labeled with an enzyme selected from the group consisting of peroxidase, alkaline phosphatase, and β-D-galactosidase.

8. The sandwich enzyme immunoassay of claim 4, wherein said determining of step (e) is performed by colorimetry, fluorometry, bioluminescence, or chemiluminescence.

9. A method for diagnosing rheumatoid arthritis in a subject, comprising determining the amount of active stromelysin and prostromelysin in a sample of blood, serum or synovial fluid obtained from the subject by said sandwich enzyme immunoassay of claim 4, and comparing said amount with that determined in normal subjects, wherein an elevated amount of active stromelysin and/or prostromelysin in the sample is indicative of rheumatoid arthritis in said subject.

* * * * *

UNITED STATES PATENT AND TRADEMARK OFFICE
CERTIFICATE OF CORRECTION

PATENT NO. : 5,834,212
DATED : November 10, 1998
INVENTOR(S) : Okada et al.

It is certified that error appears in the above-indentified patent and that said Letters Patent is hereby corrected as shown below:

Title page, item

--[73] Assignee: Fuji Yakuhin Kogyo Kabushiki Kaisha, Toyama-ken, Japan--

Signed and Sealed this

Twenty-fourth Day of August, 1999

Attest:

Q. TODD DICKINSON

Attesting Officer

Acting Commissioner of Patents and Trademarks